United States Patent [19]
Oka

[11] Patent Number: 5,854,066
[45] Date of Patent: Dec. 29, 1998

[54] METHOD FOR PRODUCING POTATO MICROTUBERS

[75] Inventor: Ichiro Oka, Shizuoka, Japan

[73] Assignee: Japan Tobacco Inc., Tokyo, Japan

[21] Appl. No.: 750,177

[22] PCT Filed: Feb. 6, 1996

[86] PCT No.: PCT/JP96/00243

§ 371 Date: Dec. 2, 1996

§ 102(e) Date: Dec. 2, 1996

[87] PCT Pub. No.: WO96/31114

PCT Pub. Date: Oct. 10, 1996

[30] Foreign Application Priority Data

Apr. 3, 1995 [JP] Japan ..................... 7-99481

[51] Int. Cl.⁶ .............. C12N 5/00; A01C 1/00; A01G 1/00
[52] U.S. Cl. .............. 435/429; 435/420; 47/58; 800/200
[58] Field of Search .................... 435/420, 429; 47/58; 800/200

[56] References Cited

U.S. PATENT DOCUMENTS 5,034,327 7/1991 Takayama et al. .............. 435/429
5,498,541 3/1996 Oka et al. .................... 435/429

FOREIGN PATENT DOCUMENTS 0476141 3/1991 European Pat. Off. .
0655192 11/1993 European Pat. Off. .

OTHER PUBLICATIONS

Estrada et al. (1986) *Plant Cell, Tissue and Organ Cultures* 7:3–10.
Torres et al. (1972) *Potato Res. 15*, pp. 76–80.
Torres et al. (1973) *Potato Res. 16* pp. 73–79.
Hussey et al., (1984) *Annals of Botany 53*, pp. 565–578.
Koller et al., (1988) *American Potato Journal 65*, pp. 528–534.
Mingo–Castel et al., (1974) *Plant Physiol. 53*, pp. 798–801.
Mingo–Castel et al. (1976) *Plant Physiol. 57*, pp. 480–485.
Perl et al. (1980) *Plant Cell Reports 7*, pp. 403–406.
Stallknecht et al. (1982) *American Potato Journal: 59*, pp. 17–32.
Wang et al. (1982) *American Potato Journal 59*, pp. 33–37.
P. H. Li (1985) *Potato Physiology 15*, pp. 503–577.

*Primary Examiner*—Leon B. Lankford, Jr.
*Assistant Examiner*—Christopher R. Tate
*Attorney, Agent, or Firm*—Birch, Stewart, Kolasch & Birch, LLP

[57] ABSTRACT

A large quantity of potato microtubers can be produced easily and in a short period of time by a method of production comprising a first step wherein potato plants are cultured in a medium with a relatively low sugar concentration under a relatively large quantity of light irradiation per day and a second step wherein the resultant potato plants are cultured in a medium with a relatively high sugar concentration under a relatively small quantity of light irradiation per day, the culture in the first step being carried out in the presence of exogenous ethylene and the culture in the second step being carried out in the absence of exogenous ethylene.

16 Claims, 2 Drawing Sheets

METHOD FOR PRODUCING POTATO MICROTUBERS

CROSS-REFERENCE TO RELATED APPLICATION

This application is the national phase under 35 U.S.C. § 371 of PCT International Application No. PCT/JP96/00243 filed on Feb. 6, 1996, which designated the United States.

TECHNICAL FIELD

The present invention relates to a method for producing potato microtubers (hereinafter sometimes referred to as "MT").

BACKGROUND ART

Conventional methods for producing potato (*Solanum tuberosum L.*) microtubers which have been widely employed comprise two steps i.e., a shoot propagation step and a tuber formation step [Wang et al., (1982) American Potato Journal 59:33–37; Hussey et al., (1984) Annals of Botany 53:565–578; and Estrada et al., (1986) Tissue and Organ Culture 7:3–10]. The shoot propagation step is a step in which virus-free potato plants are cultured in a medium with a low sugar concentration (1–3%) under light conditions to thereby propagates shoots. The tuber formation step is a step in which plants obtained in the shoot propagation step are cultured in a medium with a high sugar concentration (5–10%) under dark conditions (or under a low luminous intensity or short-day conditions) to thereby form tubers.

In order to promote tuberization, plant hormones such as cytokines have been usually added to media. For example, Wang et al. have added benzyladenine (BA) and Hussey et al. and Estrada et al. have added benzylaminopurine (BAP) and 2-chloroethyl trimethylammonium chloride (CCC) to the media.

According to these methods, however, the production efficiency of microtubers is low and the number of obtained microtubers is the same as or less than the number of plant materials cultured. Furthermore, the size of the thus obtained microtubers is fairly small. For example, in the method of Wang et al. which is frequently referred to as a method of mass-production of microtubers, only 48.6 microtubers totaling about 10 g (0.2–0.3 g/microtuber) were obtained per 100 plant materials used at the maximum. Further, a long period of about 4 months was needed for the culture. And, Estrada et al. obtained only 20.8 microtubers of about 5 mm in diameter (0.1–0.2 g) per 30 nodal cuttings of the potato plant materials used.

Since the production efficiency of the conventional microtuber production technology is low as described above, the production cost is high and this technology has not yet reached a practical level. Therefore, the microtuber production technology is now utilized only in limited uses such as the preservation or distribution of a germ plasm.

SUMMARY OF THE INVENTION

It is an object of the invention to provide a method for producing microtubers which are highly suitable for cultivation in the field easily and in large quantities.

The present inventor has studied the effects of various plant hormones and growth regulators upon the production of microtubers. As a result, it has been found that ethylene or 2-chloroethyl phosphonic acid (product name: Ethrel) which is an ethylene-generating agent increases the efficiency of microtuber production. Thus, the present invention has been achieved. Since ethylene and 2-chloroethyl phosphonic acid were believed to generally inhibit the tuberization, [Mingo-Castel et al., (1974) Plant Physiol. 53:798–801; Mingo-Castel et al., (1976) Plant Physiol. 57:480–485; Hussey et al., (1984) Annals of Botany 53:565–578; and Wang et al., (1985) Potato Physiology, Chapter 15], it was surprising that these substances give favorable effects upon tuberization.

The present invention relates to a method for producing potato microtubers comprising a first step wherein potato plants are cultured in a medium with a relatively low sugar concentration under a relatively large quantity of light irradiation per day and a second step wherein the resultant potato plants are cultured in a medium with a relatively high sugar concentration under a relatively small quantity of light irradiation per day, the culture in the first step being carried out in the presence of exogenous ethylene and the culture in the second step being carried out in the absence of exogenous ethylene.

DETAILED DESCRIPTION OF THE INVENTION

Figure 1:
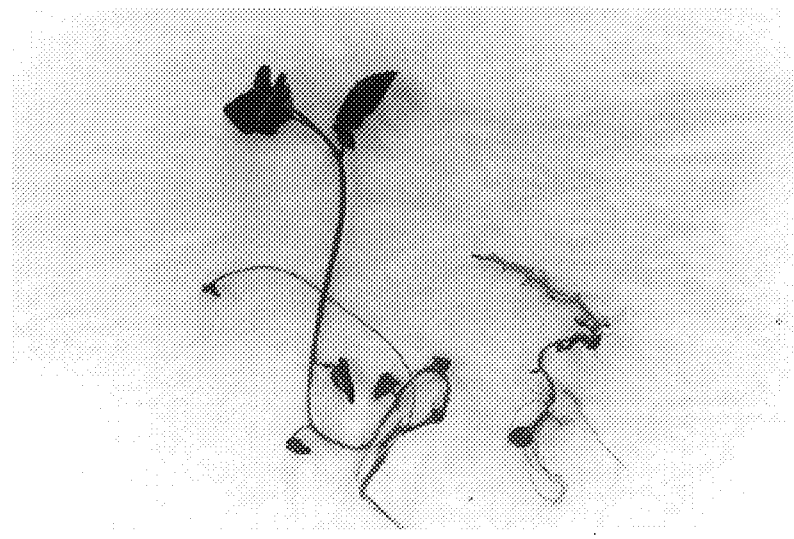
FIG. 1 is a photograph showing the morphology of a potato plantlet cultured in the presence of exogenous ethylene and the morphology of a potato plantlet cultured in the absence of exogenous ethylene.

Hereinbelow, the present invention will be described in detail.

1) First Step

The first step in the present invention is a culture step which is almost similar to the shoot propagation step of Wang et al. and refers to a step in which culture is carried out using a medium with a relatively low sugar concentration and under a relatively large quantity of light irradiation per day. The term "relatively" used herein means "when compared to the cultivation step before or after the subject step". In the first step, this term means "when compared to the second step". In the first step, potato shoots themselves are grown in order to increase mainly the number of the axillary bud (i.e., the buds contained in each node) which is necessary for the second step.

[Culture in the Presence of Exogenous Ethylene]

In the first step of the present invention, culture is carried out in the presence of exogenous ethylene. "Exogenous ethylene" means ethylene other than that generated from plants (endogenous ethylene). The condition in which exogenous ethylene is present may be produced by applying ethylene itself to the vessel for culture, but usually this condition is produced by mixing 2-chloroethyl phosphonic acid, an ethylene-generating agent, into the medium at the time of its preparation, or adding this agent to the medium when the plant materials are placed into the culture vessels or during culture.

2-Chloroethyl phosphonic acid may be added to the medium at any time from the beginning of the first step to immediately before the completion of this step. Preferably, it is added between the beginning of the first step and one week before the completion of this step. The amount of 2-chloroethyl phosphonic acid added is adjusted so that the 2-chloroethyl phosphonic acid concentration in the medium ranges from 0.05 to 50 ppm, preferably from 0.2 to 10 ppm. However, the addition of 2-chloroethyl phosphonic acid to the medium may delay the growth of the plants and, as a result, may reduce the number of microtubers produced. Therefore, when small plant materials such as single node cuttings from in vitro plantlets are used, it is preferable to add 2-chloroethyl phosphonic acid to the medium between two and four weeks from the beginning of the culture when the plants have been grown up to a considerable extent. If 2-chloroethyl phosphonic acid is added to the medium when the plants have not yet been grown sufficiently, it is preferred that this compound be added at a concentration of 1 ppm or less in the medium.

[Other Culture Conditions]

The first step of the invention may be carried out in a similar manner to that employed in the common shoot propagation step with respect to various conditions including sugar concentration and light conditions, except that the cultivation is carried out in the presence of exogenous ethylene.

As to the plant material to be used, plantlets grown by tissue culture or the like which are infected with neither viruses nor other diseases are used. These plantlets as they are (without cutting) or these plantlets cut into single node cuttings, each of which containing an axillary bud and a leaf (or into two or more nodes), are placed in a vessels containing the medium, and shoots are propagated at 18°–25° C. (preferably 18°–22° C.), at 3,000–10,000 luxes (preferably 4,000–6,000 luxes) in luminous intensity, under the lighting of 12–24 hours (preferably 16–24 hours) per day (under long daylength) using liquid-aeration culture.

As to the culture vessels, any vessel may be used as long as it transmits light and is air-tight. Generally, a bottle or culture vessel made of transparent glass, a polycarbonate culture vessel and the like are used. As to the medium, a medium obtained by adding to a tissue culture medium, such as Linsmaier & Skoog medium (1965, Physiol Plant 18:100–127, hereinafter sometimes referred to as "LS medium"), Murashige & Skoog medium (1962, Physiol Plant 15:473–497) and White's medium (1963, The Cultivation of Animal and Plant Cells), 1–3% of sucrose as a carbon source (pH 5–7, preferably 5.5–6.5, hereinafter sometimes referred to as the "shoot propagation medium") is used. As a carbon source, glucose, fructose, maltose or the like may be used instead of sucrose.

The number of plant materials placed per one liter of the vessel capacity is 0.5–5 plantlets (preferably 1–3 plantlets) or 1–10 nodal cuttings (preferably 2–4 nodal cuttings) if nodal cuttings are used. The amount of the medium per one liter of the vessel capacity is 0.1–0.5 liter (preferably 0.2–0.4 liter). The amount of aeration is 0.1–0.5 liter/liter of the vessel capacity·min (preferably 0.2–0.4 liter/liter of the vessel capacity·min). Air is blown into the liquid medium near the bottom of the container.

Usually, the height of the plants reaches about 80% of the height of the vessel in 3 to 6 weeks. However, depending on the plant material used or the amount of ethylene added, the growth of the plants may be somewhat delayed.

[Characteristic of the Plants Obtained in This Step]

By culturing in the presence of exogenous ethylene, plants can be obtained which have a number of apical buds and axillary buds bending like a hook at their ends, having small leaves and a slightly thick stem and resembling stolons in morphology.

Figure 2:
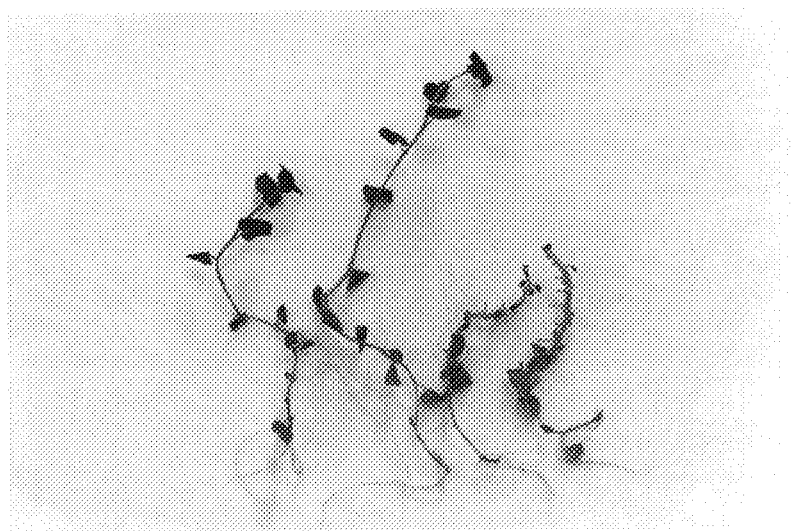
FIG. 2 is a photograph showing the morphology of potato plantlets cultured in the presence of exogenous ethylene and the morphology of potato plantlets cultured in the absence of exogenous ethylene.
Figure 3:
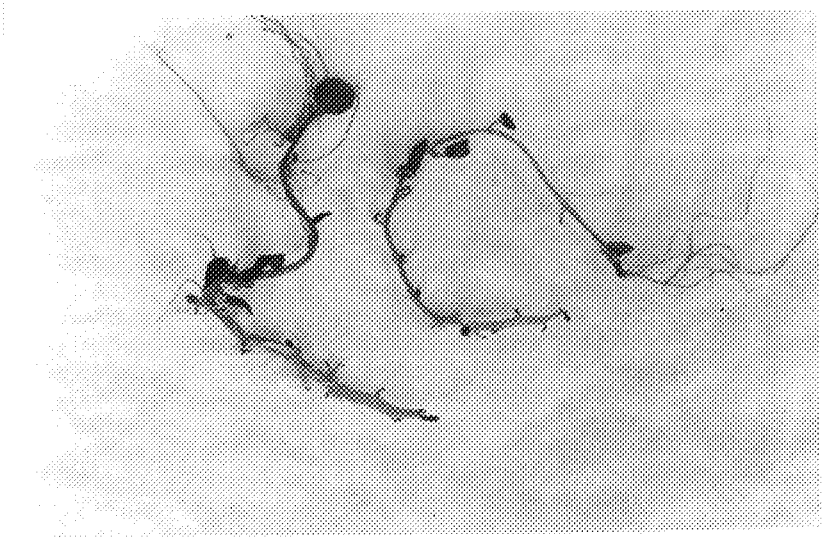
FIG. 3 is a photograph showing the morphology of potato plantlets cultured in the presence of exogenous ethylene.
Figure 4:
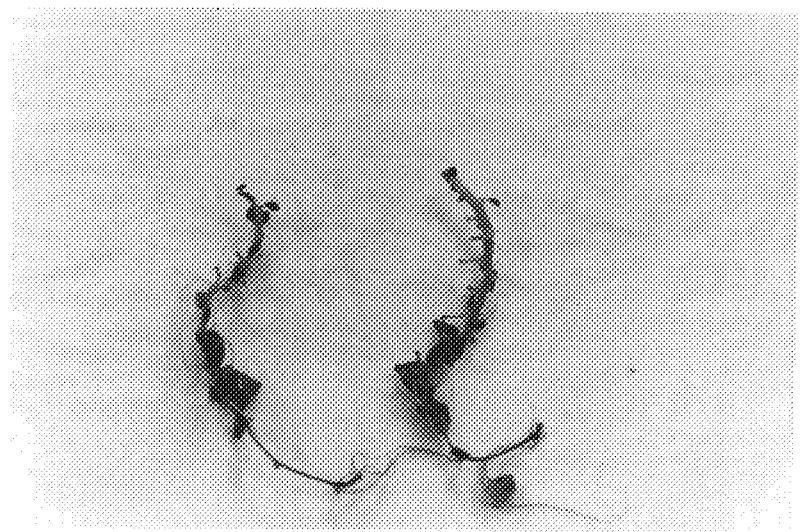
FIG. 4 is a photograph showing the morphology of potato plantlets cultured in the presence of exogenous ethylene.

FIGS. 1 and 2 are photographs showing the appearance of plants obtained by culturing in the presence of exogenous ethylene and that of plants obtained by culturing in the absence of exogenous ethylene. The left side plant in FIG. 1 and the left side plants in FIG. 2 were cultured in the absence of exogenous ethylene. The right side plant in FIG. 1 and the right side plants in FIG. 2 were cultured in the presence of exogenous ethylene. FIGS. 3 and 4 are zoomed photographs showing plants obtained by culturing in the presence of exogenous ethylene.

Generally, a tuber is formed as a result of the thickening of the end of a stolon elongated from a node. Therefore, those stolon-like apical buds and axillary buds described above are believed to be in conditions under which tubers are easily formed. However, usually tubers are not formed in the first step. When plants are cultured under conditions wherein the vessel is tightly closed and gas-exchange with outside air is prevented, plants having the above-mentioned morphology might be obtained. However, in the case of aeration culture, plants with such a morphology cannot usually be obtained if cultured in the absence of exogenous ethylene.

2) Second Step

The second step of the present invention is a culture step which is almost similar to the tuberization step of Wang et al. and refers to a step in which culture is carried out using a medium with a relatively high sugar concentration and under a relatively small quantity of light irradiation per day. The term "relatively" used herein means "when compared to the culture step before or after the subject step". In the second step, this term means "when compared to the first step". In the second step, microtubers are formed and thickened on stems elongated mainly from those axillary buds included in the shoots grown in the first step.

The second step of the present invention does not require a special method. It can be carried out as described below according to conventional methods with respect to various conditions including sugar concentration and light conditions.

When the height of the plants has reached about 50% or more (preferably 80% or more) of the height of the vessel in the first step, the remaining shoot propagation medium is removed and a medium obtained by changing the sugar concentration of the shoot propagation medium to 6–10% (hereinafter sometimes referred to as the "tuber formation medium") is added in an amount of 0.1–0.5 liter (preferably 0.2–0.4 liter) per one liter of the vessel capacity. Then, the plants are cultured in the dark or under short daylength conditions in which lighting hours are 12 hours or less (preferably 8 hours or less) per day for 3–10 weeks (preferably for 5–8 weeks) to thereby form tubers. Except the lighting conditions, other culture conditions such as temperature and the amount of aeration are the same as in the first step.

BEST MODE FOR CARRYING OUT THE INVENTION

[Example 1]

As plant materials, virus-free potato plantlets which had been grown in glass test tubes (2.5 cm in diameter, 12 cm in length) or plastic petri dishes (9 cm in diameter, 2 cm in height) according to a known method [Hussey et al., (1981) Annals of Botany 48:787–796] were used (variety: Toyoshiro; propagated from in vitro plantlets stored at Japan Tobacco Inc. Plant Breeding and Genetics Research Laboratory). Those plantlets grown in the test tube (hereinafter sometimes referred to as the "test tube-plantlets") were about 8–10 cm in length and had about 5–10 leaves. Those plantlets grown in the plastic petri dish (hereinafter sometimes referred to as the "petri dish-plantlets") were about 3–5 cm in length and had about 5–8 leaves.

The test tube-plantlets were cut into single node cuttings, each of which contained a leaf and an axillary bud, and the petri dish-plantlets were used without cutting. Eight nodal cuttings of the test tube plantlets or 5 petri dish plantlets were separately placed per one glass bottle about 12 cm in diameter, about 21 cm in height and about 1.8 liters in capacity (soled by Nippon Glass Co., Ltd.; hereinafter sometimes referred to as the "2 L bottle") containing 0.6 liter of the shoot propagation medium (LS medium+sucrose 3%, pH 5.8). The plants were cultured at 20° C., at about 4,000 luxes in luminous intensity (white fluorescent light), under lighting for 16 hours per day and under aeration of 0.4–0.5 liter/min.

Two weeks after the start of the culture, a commercial 2-chloroethyl phosphonic acid (2-chloroethyl phosphonic acid content: 10%; soled by Nissan Chemical Industries Co., Ltd.) was diluted with water to ¹⁄₁₀₀ and sterilized with filter. About 0.3 ml of the resultant solution was added to the vessel (the 2-chloroethyl phosphonic acid concentration in the medium was about 0.5 ppm) and the culture was continued under the same conditions as described above.

Several days after the addition of 2-chloroethyl phosphonic acid, the end of the apical buds and axillary buds of the plants began to bend like a hook at their ends, and newly formed leaves were small. Thus, these buds took a stolon-like morphology. Further, at the completion of this step it was observed that the number of axillary buds was fairly greater than the number in the bottles containing no added 2-chloroethyl phosphonic acid. The growth of plants in the plots where 2-chloroethyl phosphonic acid was added was slightly delayed compared to the growth in the bottles containing no added 2-chloroethyl phosphonic acid.

Thirty-seven days after the start of the culture, the medium remaining in the bottle was removed and replaced with 0.6 liter of the tuber formation medium (LS medium+sucrose 8%, pH 5.8). At that time, in order to examine the effects of 2-chloroethyl phosphonic acid at the stage of tuberization, 0.3 ml of a 100-fold dilution of the commercial 2-chloroethyl phosphonic acid was added to a part of the bottles in which nodal cuttings from the test tube-plantlets were cultured (and to which no 2-chloroethyl phosphonic acid had been added at the stage of shoot propagation).

After the medium exchange, tuberization was carried out in the dark. In the bottle in which 2-chloroethyl phosphonic acid had not been added, stolons began to thicken about 1 week after the shift to the dark conditions. On the other hand, in those bottles which 2-chloroethyl phosphonic acid had been added at the shoot propagation stage, stolons began to thicken 2 or 3 days after the shift to the dark. Tubers were harvested 40 days after the shift to the dark.

The number and weight of tubers produced per bottle are shown in Table 1.

TABLE 1

Effects of the Addition of 2-Chloroethyl Phosphonic Acid
(Variety: Toyoshiro)

| Treatments | | No. of MTs Produced (MTs/Bottle) | | | | No. of |
|---|---|---|---|---|---|---|
| Plant Material | Time of Addition | Total Number | ≧0.1 g | ≧0.5 g | Weight (g/Bottle) | Bottles Harvested |
| Petri Dish plantlets | Not Added | 23.7 (100) | 21.7 (100) | 14.0 (100) | 30.6 | 3 |
| | After 2 Weeks | 55.5 (234) | 44.0 (203) | 25.0 (179) | 40.8 | 2 |
| Nodal Cuttings (Test Tube-plantlets) | Not Added | 26.3 (100) | 24.5 (100) | 16.5 (100) | 36.8 | 4 |
| | After 2 Weeks | 35.7 (136) | 29.3 (120) | 17.7 (107) | 27.7 | 3 |
| | Time of Medium Exchange | 22.3 (85) | 21.7 (89) | 15.7 (95) | 32.4 | 3 |

Notes:
≧0.1 g: The number of those MTs having a weight of 0.1 g or more in the total number of MTs produced.
≧0.5 g: The number of those MTs having a weight of 0.5 g or more in the total number of MTs produced or in the number of ≧0.1 g MTs.
Figures in parentheses: Indexes when the number of MTs in the unadded plot is regarded as 100.
Weight: The total weight of those MTs which have a weight of 0.1 g or more.

In the 2-chloroethyl phosphonic acid-added plots where the petri dish plantlets were used, the total number of microtubers increased to 2.3 times as much as that of the unadded plot, and also the number of those microtubers of 0.5 g or more increased to 1.8 times. When nodal cuttings were used, such remarkable effects as seen in the cases of petri dish plantlets were not observed, but the total number of microtubers increased to 1.3 times.

On the other hand, in the plot where 2-chloroethyl phosphonic acid had been added at the time of medium exchange, the number of microtubers produced slightly decreased. As many researchers have pointed out, this fact seems to indicate that ethylene inhibits tuberization.

[Example 2]

Test tube-plantlets (3 per bottle) or petri dish plantlets (5 per bottle) of the variety May queen (both propagated from in vitro plantlets stored at Japan Tobacco Inc. Plant Breeding and Genetics Research Laboratory) were placed in a 2 L bottle and the plants were cultured under the same conditions as in Example 1.

One or two weeks after the start of the culture, a 100-fold dilution of the commercial 2-chloroethyl phosphonic acid was added to the bottle in an amount of 0.3 ml/bottle. Thirty-five days after the start of the culture, the medium was exchanged with the tuber formation medium, and 36 days after the medium exchange, microtubers were harvested.

Table 2 shows the number and weight of microtubers produced per bottle.

TABLE 2

Effects of the Addition of 2-Chloroethyl Phosphonic Acid
(Variety: May queen)

| Treatment | | No. of MTs Produced (MTs/Bottle) | | | | No. of |
|---|---|---|---|---|---|---|
| Plant Material | Time of Addition | Total Number | ≧0.1 g | ≧0.5 g | Weight (g/Bottle) | Bottles Harvested |
| Test tube-Plantlets | Unadded Plot | 73.5 (100) | 57.0 (100) | 22.0 (100) | 37.4 | 2 |
| | After 1 Week | 103.5 (142) | 75.0 (132) | 24.5 (111) | 39.3 | 2 |
| | After 2 Weeks | 131.0 (178) | 86.0 (151) | 35.0 (159) | 52.8 | 2 |
| Petri Dish-Plantlets | Unadded Plot | 61.3 (100) | 51.0 (100) | 25.7 (100) | 43.8 | 3 |
| | After 1 Week | 146.5 (239) | 88.0 (173) | 31.0 (121) | 47.3 | 2 |
| | After 2 Weeks | 116.0 (189) | 75.5 (148) | 32.0 (125) | 50.5 | 2 |

Notes:
≧0.1 g: The number of those MTs having a weight of 0.1 g or more in the total number of MTs produced.
≧0.5 g: The number of those MTs having a weight of 0.5 g or more in the total number of MTs produced or in the number of ≧0.1 g MTs.
Figures in parentheses: Indexes when the number of MTs in the unadded plot is regarded as 100.
Weight: The total weight of those MTs which have a weight of 0.1 g or more.

With respect to both the test tube-plantlets and the petri dish plantlets, the number of microtubers produced in the plot where 2-chloroethyl phosphonic acid had been added was apparently greater that that in the unadded plot.

[Example 3]

Test tube-plantlets of the variety Russet Burbank (propagated from in vitro plantlets stored at Japan Tobacco Inc. Plant Breeding and Genetics Research Laboratory) were placed in 2 L bottles (3 plantlets/bottle) and the plants were cultured under the same conditions as in Example 2.

At the start of the culture and 2 weeks thereafter, a 100-fold dilution of the commercial 2-chloroethyl phosphonic acid was added to the bottle in an amount of 0.3 ml/bottle (0.5 ppm) or 0.6 ml/bottle (1 ppm). Then, the culture was carried out under the same conditions as in Example 2.

Table 3 shows the number and weight of microtubers produced per bottle.

TABLE 3

Effects of the Addition of 2-Chloroethyl Phosphonic Acid
(Variety: Russet Burbank)

| Treatments | | No. of MTs Produced (MTs/Bottle) | | | | No. of |
|---|---|---|---|---|---|---|
| Time of Addition | Amount Added | Total Number | ≧0.1 g | ≧0.5 g | Weight (g/Bottle) | Bottles Harvested |
| Unadded Plot | | 33.0 (100) | 25.5 (100) | 13.0 (100) | 18.0 | 2 |
| At the start of culture | 0.3 ml | 69.6 (209) | 54.0 (212) | 16.5 (127) | 27.6 | 2 |
| After 2 Weeks | 0.3 ml | 57.0 (173) | 48.0 (188) | 24.0 (185) | 41.0 | 2 |
| After 2 Weeks | 0.6 ml | 52.0 (158) | 42.0 (165) | 23.0 (177) | 44.5 | 1 |

Notes:
≧0.1 g: The number of those MTs having a weight of 0.1 g or more in the total number of MTs produced.
≧0.5 g: The number of those MTs having a weight of 0.5 g or more in the total number of MTs produced or in the number of ≧0.1 g MTs.
Figures in parentheses: Indexes when the number of MTs in the unadded plot is regarded as 100.
Weight: The total weight of those MTs which have a weight of 0.1 g or more.

In any of the plots where 2-chloroethyl phosphonic acid had been added, the number of microtubers produced was apparently greater than that in the unadded plot. Particularly, the number of those microtubers having a weight of 0.5 g or more was greater in those plots where the above-mentioned compound had been added 2 weeks after the start of the culture than the number in the plot where it had been added at the start of the cultivation. There was no difference in the number of microtubers produced due to the difference in the amount of 2-chloroethyl phosphonic acid added.

[Example 4]

Test tube-plantlets of the variety May queen were cut into nodal cuttings, each of which contained a leaf and an axillary bud. Eight nodal cuttings were placed per one 2 L bottle. Several amounts of diluted 2-chloroethyl phosphonic acid were added at the start of the cultivation or 4 weeks thereafter and the influence of the period of addition and the concentration of the above compound upon microtuber production were examined.

2-Chloroethyl phosphonic acid (a 100-fold dilution of the commercial 2-chloroethyl phosphonic acid) was added in an amount of 0.1 ml/bottle (0.17 ppm), 0.3 ml/bottle (0.5 ppm) or 0.6 ml/bottle (1 ppm) in the plot where the addition was made at the start of the culture. In the plot where the addition was made 4 weeks after the start of the culture, the above-mentioned dilution was added in an amount of 0.3 ml, 0.6 ml or 1.2 ml per bottle. Since the amount of the medium was reduced after 4 weeks, the 2-chloroethyl phosphonic acid concentrations in the medium are about 1–2 ppm, 0.6–1.2 ppm and 4–8 ppm, respectively. Further, in order to prevent the lowering of the pH in the medium due to the addition of 2-chloroethyl phosphonic acid, the 2-chloroethyl phosphonic acid solution was added after the adjustment of its pH to about 5. Although 2-chloroethyl phosphonic acid is stored at a low pH for the prevention of decomposition, it is preferred that the pH of the 2-chloroethyl phosphonic acid solution be 5 or more for the purpose of the generation of ethylene through decomposition.

The culture was carried out under the same conditions as in Example 1. Thirty-six days after the start of the culture, the medium was exchanged, and 45 days after the medium exchange, microtubers were harvested.

Table 4 shows the number and weight of microtubers produced per bottle.

the start of the culture, the number of microtubers produced in any of the three plots was greater than the number in the unadded plot.

In those plots where 2-chloroethyl phosphonic acid has been added, the growth of plants is delayed. The degree of this delay varies depending on the 2-chloroethyl phosphonic acid concentration and the state of plant materials, particularly the size of plants. Since nodal cutting from in vitro plantlets were used for this experiment, the growth of plants was remarkably delayed in the plots where 2-chloroethyl phosphonic acid had been added at high concentrations at the start of the culture. For this reason, the number of microtubers produced in these plots was smaller than the number in the unadded plot. When a small material such as a nodal cutting is used as a plant material, it is preferred that 2-chloroethyl phosphonic acid be added at a low concentration or after shoots have been grown to a considerable extent.

[Example 5]

Two test tube-plantlets of the variety Nohrin No. 1 (propagated from in vitro plantlets stored at Japan Tobacco Inc. Plant Breeding and Genetics Research Laboratory) were placed per one 2 L bottle, and the plants were cultured under the same conditions as in Example 1 except that 500 ml of the shoot propagation medium was used per one bottle.

At the start of the culture or 2 weeks thereafter, a 100-fold dilution of the commercial 2-chloroethyl phosphonic acid was added in an amount of 0.25 ml/bottle (0.5 ppm). Thirty-five days after the start of the culture, the medium was exchanged with the tuber formation medium, and 35 days after the medium exchange, microtubers were harvested.

TABLE 4

Effects of the Addition of 2-Chloroethyl Phosphonic Acid
(Variety: May queen)

| Treatment | | No. of MTs Produced (MTs/Bottle) | | | | No. of |
|---|---|---|---|---|---|---|
| Time of Addition | Amount Added | Total Number | ≧0.1 g | ≧0.5 g | Weight (g/Bottle) | Bottles Harvested |
| Unadded Plot | (control) | 49.0 (100) | 43.5 (100) | 26.0 (100) | 46.7 | 2 |
| At the start of culture | | 69.0 (141) | 52.0 (120) | 25.7 ( 99) | 46.4 | 3 |
| At the start of culture | 0.3 ml | 31.0 ( 63) | 25.7 ( 59) | 13.7 ( 53) | 18.6 | 3 |
| At the start of culture | 0.6 ml | 17.5 ( 36) | 13.5 ( 31) | 5.5 ( 21) | 9.1 | 2 |
| After 4 Weeks | 0.3 ml | 57.5 (117) | 51.5 (118) | 33.0 (127) | 59.1 | 2 |
| After 4 Weeks | 0.6 ml | 66.0 (135) | 47.3 (109) | 26.7 (103) | 43.6 | 3 |
| After 4 Weeks | 1.2 ml | 51.7 (106) | 46.7 (107) | 30.0 (115) | 46.5 | 3 |

Notes:
≧0.1 g: The number of those MTs having a weight of 0.1 g or more in the total number of MTs produced.
≧0.5 g: The number of those MTS having a weight of 0.5 g or more in the total number of MTs produced or in the number of ≧0.1 g MTs.
Figures in parentheses: Indexes when the number of MTs in the unadded plot is regarded as 100.
Weight: The total weight of those MTs which have a weight of 0.1 g or more.

When 2-chloroethyl phosphonic acid had been added at the start of the culture, the number of microtubers produced in the 0.1 ml plot was greater than the number in the unadded plot, but the numbers in the 0.3 ml and 0.6 ml plots were smaller than the number in the unadded plot. When 2-chloroethyl phosphonic acid had been added 4 weeks after Table 5 shows the number and weight of microtubers produced per bottle.

In Nohrin No. 1, also the number of microtubers produced in any of the treated plots (added at the start of the culture or 2 weeks thereafter) was fairly greater than the number in the unadded plot.

TABLE 5

Effects of the Addition of 2-Chloroethyl Phosphonic Acid
(Variety: Nohrin No. 1)

| Time of Addition | No. of MTs Produced (MTs/Bottle) | | | Weight (g/Bottle) | No. of Bottles Harvested |
|---|---|---|---|---|---|
| | Total Number | ≧0.1 g | ≧0.5 g | | |
| Not Added | 16.3 (100) | 15.7 (100) | 11.7 (100) | 23.9 | 3 |
| At the start of culture | 27.0 (165) | 22.0 (140) | 12.0 (103) | 15.3 | 1 |
| After 2 Weeks | 24.0 (147) | 23.0 (147) | 16.5 (141) | 34.9 | 2 |

Notes:
≧0.1 g: The number of those MTs having a weight of 0.1 g or more in the total number of MTs produced.
≧0.5 g: The number of those MTs having a weight of 0.5 g or more in the total number of MTS produced or in the number of ≧0.1 g MTs.
Figures in parentheses: Indexes when the number of MTS in the unadded plot is regarded as 100.
Weight: The total weight of those MTs which have a weight of 0.1 g or more.

[Example 6]

The effects of the addition of 2-chloroethyl phosphonic acid and ethylene upon microtuber production were examined on the three varieties of Toyoshiro, May queen and Russet Burbank.

As to Toyoshiro and May queen, three test tube-plantlets were transplanted per one 2 L bottle. As to Russet Burbank, two test tube-plantlets were transplanted per one 2 L bottle. (All of these test tube-plantlets of the three varieties were propagated from in vitro plantlets stored at Japan Tobacco Inc. Plant Breeding and Genetics Research Laboratory.) The plants were cultured under the same conditions as in Example 1 except that 500 ml of the shoot propagation medium was used per one bottle.

In those plots to be treated with 2-chloroethyl phosphonic acid, a 100-fold dilution of the commercial 2-chloroethyl phosphonic acid was added 2 weeks after the start of the culture in an amount of 0.25 ml/bottle (0.5 ppm).

On the other hand, ethylene was added by aeration into the culture bottle through another 2 L bottle (different from the culture bottle) containing 500 ml of a 1000-fold dilution of the commercial 2-chloroethyl phosphonic acid from 2 weeks and 4 weeks after the start of the culture. In order to promote the release of ethylene from 2-chloroethyl phosphonic acid, the pH of the 2-chloroethyl phosphonic acid solution was adjusted at about 5.5 after dilution. In the aeration to the bottle containing the 2-chloroethyl phosphonic acid solution, air was blown into the solution. In these plots treated with ethylene, aeration was carried out through the above solution until the time of the medium exchange. Thirty-five days after the start of the culture, the medium was exchanged with the tuber formation medium, and 35 days after the medium exchange, microtubers were harvested.

Table 6 shows the number and weight of microtubers produced per bottle.

In both ethylene-added plots and 2-chloroethyl phosphonic acid added plots, the number of microtubers produced was greater than the number in the unadded plot. Further, the addition of 2-chloroethyl phosphonic acid was more effective than the addition of ethylene.

TABLE 6

Effects of the Addition of 2-Chloroethyl Phosphonic Acid and Ethylene
(Varieties: Toyoshiro, May Queen and Russet Burbank)

| Variety | Time of Addition | No. of MTs Produced (MTS/Bottle) | | | Weight (g/Bottle) | No. of Bottle Harvested |
|---|---|---|---|---|---|---|
| | | Total Number | ≧0.1 g | ≧0.5 g | | |
| Toyoshiro | Not Added | 14.0(100) | 13.0(100) | 9.5(100) | 20.7 | 2 |
| | After 2 Weeks* | 33.3(238) | 23.7(182) | 9.7(102) | 13.8 | 3 |
| | After 2 Weeks** | 17.5(125) | 16.0(123) | 6.5(68) | 9.8 | 2 |
| | After 4 Weeks** | 15.3(109) | 14.0(107) | 10.0(105) | 17.5 | 3 |
| May Queen | Not Added | 22.3(100) | 21.3(190) | 15.3(100) | 27.8 | 4 |
| | After 2 Weeks* | 40.3(181) | 30.3(142) | 16.5(108) | 34.8 | 4 |
| | After 2 Weeks** | 29.3(132) | 24.7(116) | 12.3(81) | 22.8 | 3 |
| | After 4 Weeks** | 28.3(127) | 24.0(113) | 14.5(95) | 24.8 | 4 |
| Russet Burbank | Not Added | 19.3(100) | 16.3(100) | 11.0(100) | 18.5 | 4 |
| | After 2 Weeks** | 39.0(203) | 33.3(205) | 14.7(133) | 18.1 | 3 |

Notes:
*: 2-Chloroethyl phosphonic acid-added plot.
**: Ethylene-added plot.
≧0.1 g: The number of those MTs having a weight of 0.1 g or more in the total number of MTs produced.
≧0.5 g: The number of those MTs having a weight of 0.5 g or more in the total number of MTs produced or in the number of ≧0.1 g MTs.
Figures in parentheses: Indexes when the number of MTS in the unadded plot is regarded as 100.
Weight: The total weight of those MTs which have a weight of 0.1 g or more.

EFFECT OF THE INVENTION

Compared to conventional methods, the method of the invention makes it possible to produce a larger quantity of microtubers easily and in a short period of time. Furthermore, the resultant microtubers are big in size and thus excellent in cultivatability in the field. Therefore, the present invention is an extremely useful technology from an industrial point of view.

What is claimed is:

1. In a method for producing potato microtubers, comprising a first step of shoot propagation wherein virus-free potato plantlets are cultured in a medium with a relatively low sugar concentration under a relatively large quantity of light irradiation per day, and a second step of tuber formation wherein the resultant potato plants are cultured in a medium with a relatively high sugar concentration under a relatively small quantity of light irradiation per day, the improvement comprising the culturing in the first step being carried out in the presence of an effective shoot-propagating amount of exogenous ethylene supplied by an ethylene-generating agent, and the culturing in the second step being carried out in the absence of exogenous ethylene.

2. The method of claim 1, wherein said ethylene generating agent is 2-chloroethyl phosphoric acid.

3. The method of claim 2, wherein the concentration of 2-chloroethyl phosphonic acid in the medium in said first step is from 0.05 to 50 ppm.

4. The method of claim 1, wherein said ethylene generating agent is added to said medium before said first step.

5. The method of claim 1, wherein said ethylene generating agent is added to said medium during said first step and between two and four weeks after the beginning of culturing of said virus-free plantlets.

6. The method of claim 1, wherein each liter of vessel capacity contains 0.5–5 plantlets or 1–10 nodal cuttings.

7. The method of claim 1, wherein said plantlets are petri dish plantlets.

8. The method of claim 1, wherein said plantlets are test-tube plantlets.

9. The method of claim 1, wherein said plantlets are nodal cuttings.

10. The method of claim 1, wherein said potato plantlets are variety Toyoshiro.

11. The method of claim 1, wherein said potato plantlets are variety May queen.

12. The method of claim 1, wherein said potato plantlets are variety Russet Burbank.

13. The method of claim 1, wherein said potato plantlets are variety Nohrin No. 1.

14. The method of claim 1, wherein said potato plantlets are nodal cuttings comprising a leaf and an axillary bud.

15. The method of claim 1, wherein the pH of the medium is maintained at about 5 or more during said first step.

16. The method of claim 1, wherein said medium in said shoot propagation step is aerated.

* * * * *